United States Patent [19]

Morrison

[11] 4,172,979

[45] Oct. 30, 1979

[54] METHOD AND APPARATUS FOR AUTOMATICALLY PROVIDING RADIATION THERAPY TREATMENT CONFORMING TO A DESIRED VOLUME OF TISSUE

[76] Inventor: Richard A. Morrison, 9021 Delmar, Shawnee Mission, Kans. 66207

[21] Appl. No.: 915,996

[22] Filed: Jun. 15, 1978

[51] Int. Cl.² ............................................. G02B 5/00
[52] U.S. Cl. .................................... 250/505; 250/512
[58] Field of Search ................ 250/452, 505, 512, 513

[56] References Cited

PUBLICATIONS

"An Examination of Synchronous Shielding in Co-60 Rotational Therapy" by Rawlinson et al., Radiology, vol. 102, pp. 667–671, Mar. 1972.

Primary Examiner—Harold A. Dixon
Attorney, Agent, or Firm—Schmidt, Johnson, Hovey & Williams

[57] ABSTRACT

A device implemented method for conformation radiotherapy of tumors or the like involves sequentially interposing a plurality of separate, individual radiation beam shaping shields between a tumor and a source of radiation as the latter is rotated about the tumor in order to deliver a plurality of separate doses of radiation to various profiles of the tumor which provides uniform, homogenious radiation dosage to the tumor. The method permits use of full thickness, central radiation absorbers for completely protecting healthy organs or living tissue lying in the path of the radiation beam. A treatment reel releasably carrying a plurality of the radiation shields each having a central absorber integral therewith, in aligned relationship on the circumference thereof is removably mounted for rotation on a treatment head carrying the radiation source which is revolvable in a course around the patient. Mechanism is provided for producing incremental rotation of the reel on the head as the latter shifts between treatment locations in its revolving course, whereby the radiation shields are sequentially moved into a shielding position when the head is disposed at respectively corresponding treatment locations.

18 Claims, 11 Drawing Figures

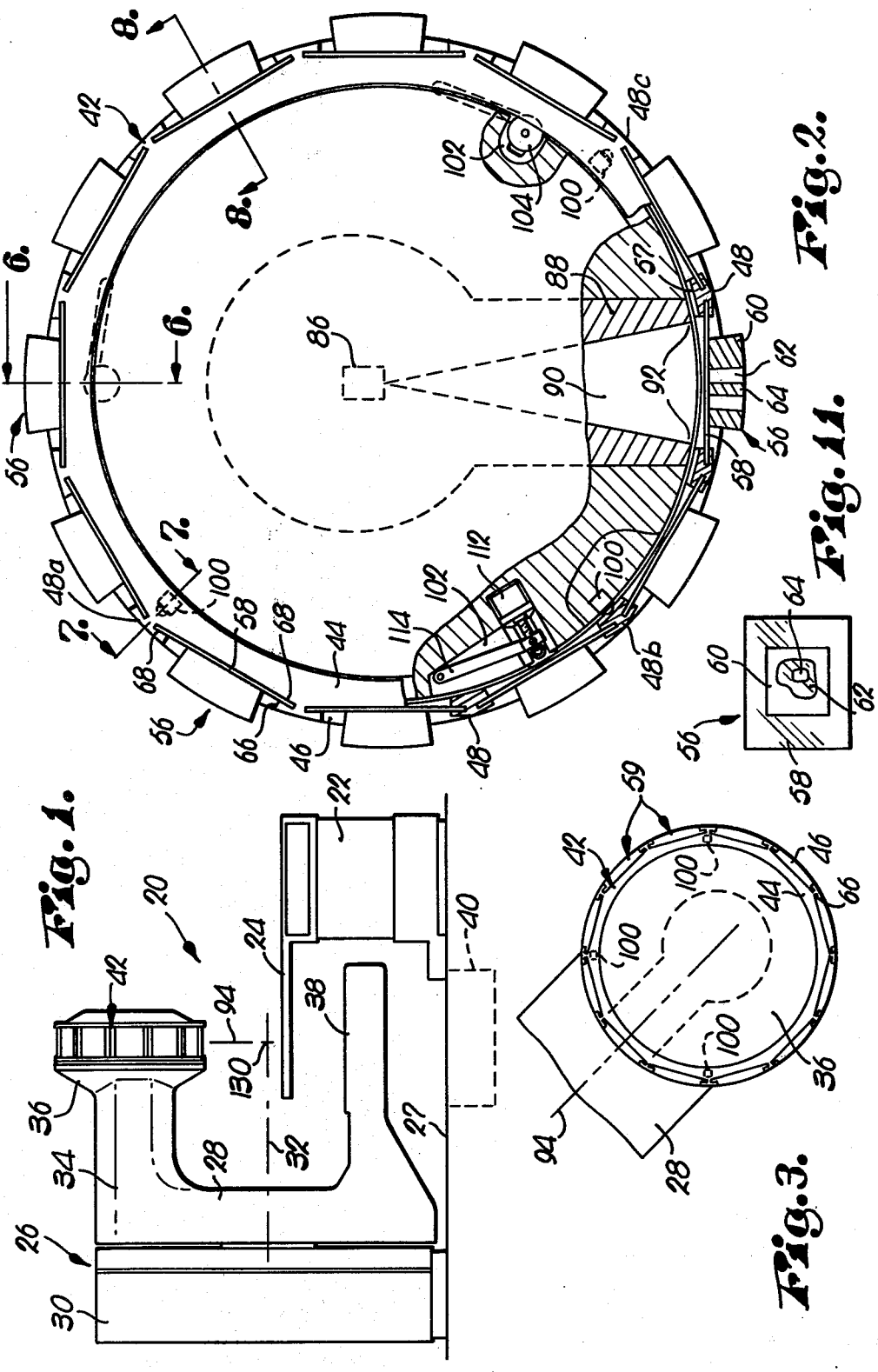

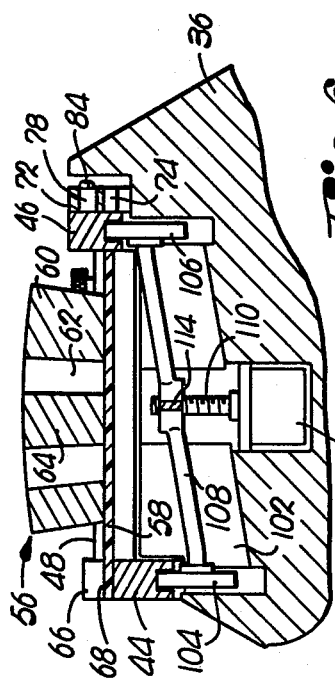
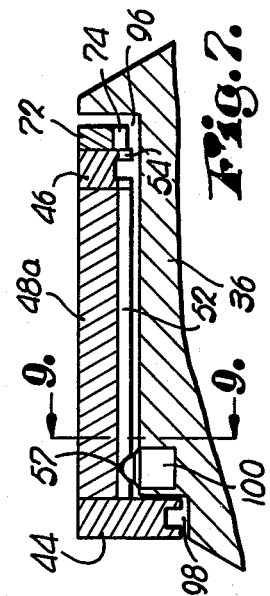
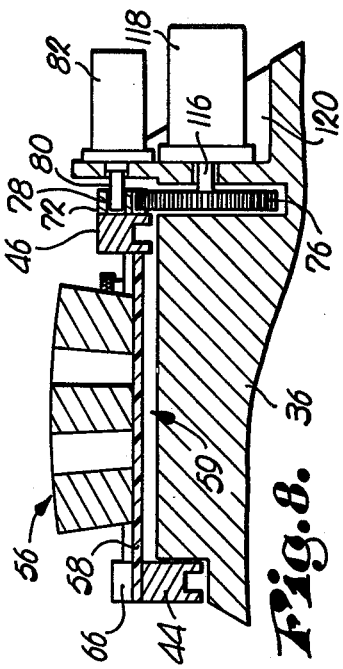
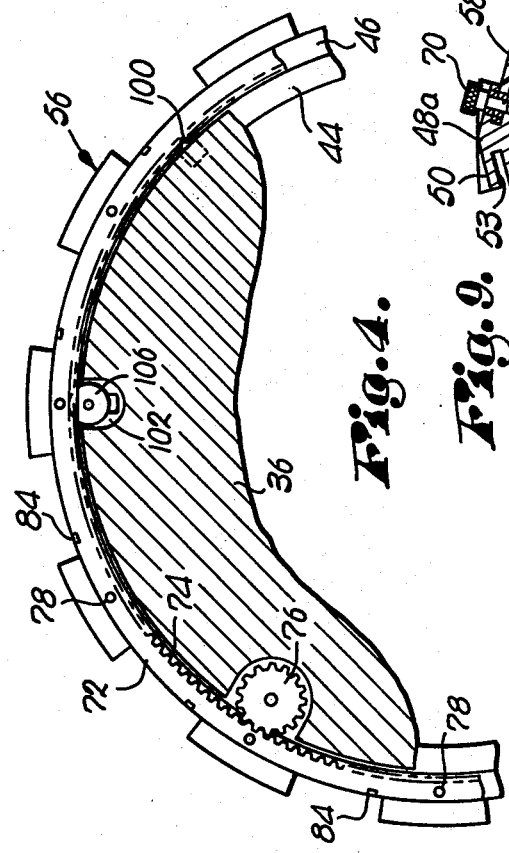
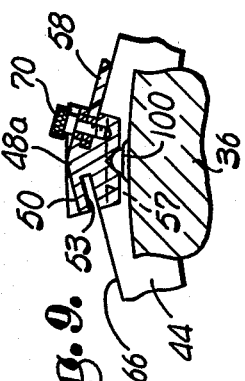
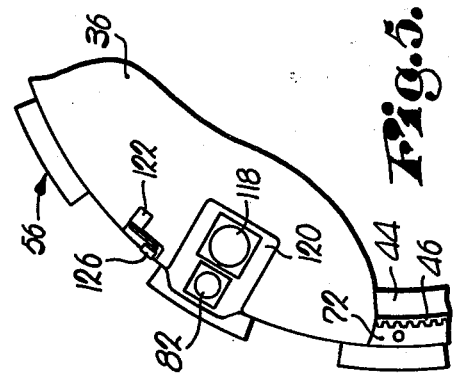

METHOD AND APPARATUS FOR AUTOMATICALLY PROVIDING RADIATION THERAPY TREATMENT CONFORMING TO A DESIRED VOLUME OF TISSUE

TECHNICAL FIELD

This invention generally deals with the treatment of living tissue using radiation, and relates more particularly to a device implemented method for providing radiotherapy treatment conforming to a desired volume of tissue in a patient.

BACKGROUND ART

The therapeutic technique of applying dosages of radiation to tumors within the human body has been practiced for some time. Usually, only a slight difference will exist in the radio sensitivities of a tumor and the surrounding healthy tissue, with the former being somewhat more sensitive than the latter. Consequently, it is an important object in conducting radiation therapy to avoid as much injury as possible to the healthy surrounding tissue while delivering a homogeneous and adequate dose to the tumor. This presents an extremely difficult problem since the tumor comprises an irregularly configured, three-dimensional shape which is often situated well into the body and thus completely surrounded by healthy tissue.

Early attempts to minimize lethal damage to the healty tissue surrounding the treated tumor involved simply directing a rectangularly-shaped beam of radiation onto the tumor and rotating the beam around the patient (and thus, around the tumor) so that the resulting volume of tissue subjected to radiation was cylindrical in shape and included the irregularly configured tumor portion therewithin. Of course, this early technique resulted in destruction of a considerable amount of normal healthy tissue surrounding and sometimes enveloped by the tumor.

A more recent approach to the problem has succeeded in confining the treated area to the volume of the tumor and is commonly known in the art as "comformation" radiotherapy. Heretofore, conformation radiotherapy has involved the use of apparatus which conforms the beam of radiation to the shape of the tumor as the latter is rotated relative to the radiation beam. One method of practicing conformation radiotherapy involves interposing a beam shaping radiation shield between the source of radiation and the tumor, and then shifting the shield in synchronization with the rotation of either the patient or the radiation beam in a manner to continuously alter the cross-sectional shape of the beam as different sides of the tumor are exposed to such beam. Various types of apparatus for producing the needed synchronized shielding which continuously alters the cross-sectional shape of the beam have been employed in the past as discussed by Shinji Takahashi in: *Conformation Radiotherapy*, Department of Radiology, Nagoya University School of Medicine, Japan, ACTA Radiologica Supplementum 242, 1965 (see Chapter III, Pages 49-66). Prior art synchronized shielding apparatus typically have employed a multiplicity of differently configured, gear-driven cam elements, often operating on corresponding, shiftable, radiation shielding segments forming a diaphragm surrounding the radiation beam source. Each of the cam elements correspond to a geometrical section of a particular tumor volume of a individual patient and must therefore be tailor made for treating a particular tumor. As the radiation beam rotates around the patient, the cam elements are sychronously driven to continuously change the diaphram in a manner to alter the cross-sectional shape of the radiation beam to conform to the profile of the tumor, as the various sides or "profiles" of such tumor are presented to the beam while the latter rotates. From the foregoing, it is clearly apparent that the prior art apparatus for practicing conformation radiotherapy was particularly complex with respect to the mechanisms that were employed, moreover, the radiotherapy method of treatment using the mentioned prior art apparatus was particularly time-consuming, and therefore inefficient, since numerous mechanisms were required to be assembled and disassembled in the course of treating different patients.

To further complicate the problems associated with conformation radiotherapy, it is necessary to devise a means of protecting radiosensitive normal tissues and organs such as the spinal cord, kidneys, ocular lens, and small intestine, which organs lie in the path of the radiation beam, between the tumor to be treated and the radiation source. The prior art method of protecting healthy organs lying in the radiation beam path involved the placement of radiation absorbing structures between the source of radiation and the patient which function to reduce or "hollow out" the dosage of radiation applied to the healthy organs. These radiation absorbing structures possessed geometrical dimensions corresponding in direct proportion to the healthy organ to be protected, and in some cases were rotated in synchronization with the rotation of the radiation source where the healthy organ was of irregular shape. These radiation absorbing protective structures, commonly known in the art as "central absorbers" due to the fact that they absorb a portion of the radiation lying within central areas of the radiation beam, were less than completely effective in protecting the healthy organ because the thickness of the prior art absorber was dictated by the cross-sectional thickness of the organ being protected. This thickness limitation is due to the fact that the prior art method of protecting healthy organs requires that the central absorber be rotated relative to the radiation beam in a manner to cause various sides of the central absorber to be presented to the radiation beam as the latter rotates around the patient. Because the thickness of the central absorber is dictated by the cross-sectional area of the organ to be protected and must be directly proportional to the latter, the thickness of the central absorber is insufficient to completely absorb the radiation impinging thereon, and consequently allows a portion of such radiation to pass therethrough and onto the organ which is intended to be protected. Since it is optimally desired to prevent any radiation whatsoever from being applied to the healty organ, the prior art method of using rotating central absorbers having cross section geometries corresponding to the organ to be protected, are less than completely effective in shielding such organ from undesired radiation treatment. Moreover, it is quite clear that the complexity of the apparatus required to practice the previous method is considerably increased by the need for mechanism to rotate one or more central absorbers in synchronization with the shiftable shielding segments which continually change the cross section configuration of the radiation beam to correspond to different profiles of the tumor, while the radiation source is rotated around the patient.

In fact, due to the excessive complexity, and therefore cost, of prior art radiotherapy apparatus of the type described above, conformation type radiotherapy using the "hollowed-out" technique has thus far enjoyed only limited use.

From the foregoing, it is readily apparent that there is a clear need in the art for a novel method of conformation radiotherapy which is considerably more efficient than prior art techniques, and which employs apparatus which reduces equipment cost and operating expenses to a level which will permit wide scale use of the conformation radiotherapy treatment method.

DISCLOSURE OF INVENTION

The present invention provides a device implemented method for practicing conformation cineradiotherapy which is highly efficient in terms of the number of patients which may be successively treated and which employs cineradiotherapy apparatus that is economical from a manufacturing standpoint while also yielding increased protection of healthy organs when using the "hollowed-out" technique of protecting healthy tissues. Conventional, radiotherapy apparatus having a radiation beam source mounted for rotation around a stationarily held patient, is adapted to have removably mounted for rotation thereon a circular treatment reel dedicated to the treatment of a particular tumor of an individual patient. The treatment reel is provided with a plurality of field shaping, radiation shields releasably held on the periphery thereof, which shields including cut-out portions corresponding to various cross-sectional profiles of the tumor to be treated and further may include a central radiation absorber disposed within the cut-out portions and corresponding in shape to the profile of a healthy organ to be protected. Each of the radiation shields, including the central absorber portions thereof, are of a thickness sufficient to almost completely preclude the passage of radiation therethrough. Gantry structure for positioning a radiation source in spaced relationship to the patient provides motorized, gear-driven, roller mounting of the treatment reel around the radiation source whereby to allow rotation of the reel around the radiation source in a manner to successively shift each of the radiation shields into a shielding position between the radiation source and the patient. With a treatment reel mounted in its operative position on the rotating gantry, the latter is rotated thereby likewise rotating the radiation source along with the reel between a plurality of discrete, treatment positions around the patient, corresponding in number to the number of radiation shields carried by the treatment reel. As the radiation source is moved to each new treatment position, thereby exposing a different profile of the tumor to such source, a different radiation shield having cut-out portions therein corresponding to the profile of the tumor then presented to the source, is shifted into shielding relationship between the source and the tumor, whereupon a predetermined dosage of radiation is delivered from the source thereof to the corresponding profile of the tumor as the gantry is rotated over a known arc, e.g. 30 degrees, to the next treatment starting position. After delivering such predetermined dosage to one profile of the tumor, the treatment reel is rotated to bring a subsequent radiation shield into the shielding position, which corresponds to the profile of the tumor next to be treated. The steps of rotating the radiation source between successive treatment positions around the patient and selectively rotating the treatment reel to interpose the various radiation shields into shielding relationship between corresponding profiles of the tumor and the radiation source, continues until the prescribed number of profiles of the tumor have all received the predetermined dosage of radiation. Inasmuch as the full thickness, central absorber needed for protecting healthy organs is provided integral with each of the plurality of radiation shields, it can be appreciated that mechanism is not required for rotating a central absorber in synchronization with the rotation of the radiation source about the patient. Upon completion of the treatment of one tumor in a patient, the associated treatment reel may be simply removed from the gantry and replaced with a second treatment reel having a plurality of radiation shields similarly mounted thereon which correspond to the various profiles of a second tumor in another patient, whereupon treatment of the second tumor may then be commenced in a manner identical to that described above.

BRIEF DESCRIPTION OF DRAWINGS

In the drawings:

FIG. 1 is a side elevational view of the cineradiotherapy device which is used in practicing the method in the present invention, and which forms the preferred embodiment of the apparatus of the present invention, shown in operative relationship to a patient supporting treatment table;

FIG. 2 is a front elevational view of the treatment head having a treatment reel mounted in operative relationship thereon, parts being broken away in section to more clearly reveal means for releasably holding the reel on the treatment head;

FIG. 3 is a fragmentary front elevational view of the cineradiotherapy device showing a treatment reel mounted in operative relationship thereon with the radiation shield assemblies having been removed from the reel, and depicted in the reel exchanging position thereof;

FIG. 4 is a fragmentary, rear view of the treatment head, parts being broken away to more clearly show the gear-driven relationship between the treatment head and a treatment reel;

FIG. 5 is a fragmentary, rear view of a portion of the treatment head depicting motorized means for rotating the treatment reel relative to the treatment head and for locking the former into a treatment position with respect to the latter;

FIG. 6 is a fragmentary, sectional view taken along the line 6—6 in FIG. 2;

FIG. 7 is a fragmentary, sectional view taken along the line 7—7 in FIG. 2;

FIG. 8 is a fragmentary, sectional view taken along the line 8—8 in FIG. 2;

FIG. 9 is a fragmentary, sectional view taken along the line 9—9 in FIG. 7;

FIG. 10 is a fragmentary, top view of a portion of the treatment head depicting a reel positioning switch and trip dog for controlling the rotational position of the treatment reel; and, FIG. 11 is a plan view of one of the radiation shield assemblies shown removed from a treatment reel, and including a central radiation absorber.

BEST MODE FOR CARRYING OUT THE INVENTION

For sake of convenience, a description of the construction of the apparatus will first be provided, followed by a discussion of the operation of the apparatus in connection with the use thereof in practicing a novel method of radiotherapy.

Referring first to FIG. 1, a cineradiotherapy system generally indicated by the numeral 20 includes a pivotal treatment table 22 of the conventional type having a horizontally extending platform 24 for supporting a patient thereupon a spaced distance above the floor 27, and further includes a cineradiotherapy treatment device generally indicated by the numeral 26. The device 26 includes a movable portion 28 which is mounted on a stationary portion 30 for rotation about a horizontally extending axis 32. The movable portion 28 includes a horizontally extending supporting structure in the nature of a gantry 34 terminating in a treatment head 36 spaced from the horizontal axis 32 and in overlapping relationship to the platform 24, while a horizontally extending radiation safety shield 38 is mounted on the opposite extremity of the movable portion 28, in spaced, opposed relationship to the treatment head 36, and aligned in a vertical plane extending through the latter. Shield 38 is made of a suitable radiation absorbing material to prevent escape of stray radiation passing from the treatment head 36 past platform 24. The stationary portion 30 of the device 26 includes conventional motorized means for producing rotational movement of the movable portion 28 about the axis 32 and may also include a suitable power supply for energizing a later discussed, suitable source of radiation mounted in the treatment head 36. A cut-out portion 40 in the floor 27 beneath the platform 24 is provided to allow clearance of the treatment head 36 upon rotation of the latter about the horizontal axis 32.

Referring now also to the remaining figures, the treatment head 36 is adapted to have removably mounted for rotation thereon a treatment reel 42. Treatment reel 42 comprises a drum-like cylindrical structure having the opposite ends thereof open and includes a front and rear flange 44 and 46 respectively having secured therebetween, by any suitable means, at equally spaced radial locations around the periphery thereof the longitudinally extending support members 48 which are formed from any suitable rigid material such as steel or the like. Each of the support members 48 include oppositely beveled, adjacent upper surface areas 50 and are further provided with longitudinally extending slots 53 on opposite sides thereof. Certain selected ones of the support members 48, such as members 48a, 48b, and 48c, include a longitudinally extending, V-shaped groove 52 in the inner surface thereof adjacent the treatment head 36 while portions of the rear flange 46 in registration with the V-shaped grooves 52 in the support members 48 are provided with V-shaped openings 54 therein for purposes which will become later apparent. Each of the members 48 also includes an arcuately shaped V-shaped groove 57 in the inner surface thereof adjacent the front flange 44 which extends in a circumferential direction around the treatment reel 42.

A plurality of radiation shield assemblies each generally indicated by the numeral 56 includes a rectangularly shaped support plate 58 comprising material which is transparent to radiation having mounted on the upper, outer surface thereof, by any suitable means such as screws or the like, an outer, radiation shield 60 having cut-out portions 62 therethrough within which there is disposed a central radiation absorber 64, likewise secured by any suitable means to the upper surface of support plate 58. Radiation shield 60 and central absorber 64 may be manufactured from any suitable material adapted to absorb and prevent the transmission therethrough of radiation. The cut-out portions 62 in the radiation shield 60 will conform in geometrical shape to a particular profile of the volume of tissue in the patient to be treated, while the central absorber 64 will likewise conform in cross-sectional shape to a healthy organ to be protected which lies between a later discussed source of radiation and the volume of tissue within the patient to be treated. The sidewalls of both the radiation shield 60 and central absorber 64 adjacent the cut-out portions 62 are slightly inclined with respect to the support plate 58 in order to prevent an undesired radiation shadowing effect on the volume of tissue to be treated, and it is important that both the radiation shield 60 and central absorber 64 be sufficiently thick to almost completely prevent the passage of radiations through the solid portions thereof. Both the radiation shields 60 and central absorber 64 may be manufactured in accordance with a method for making a focused shield disclosed in U.S. Pat. No. 3,937,971.

The front flange 44 includes a cut-out portion 66 in the periphery thereof of sufficient width to allow the passage of the radiation shields 60 therethrough, and further includes a pair of slots 68 on opposite sides of the cut-out portion 66 to complementally receive the plate 58 therethrough. Thus, slots 53 and 68 slidably receive the plate 58 therewithin and function to position and partially hold the radiation shield assembly 56 in proper alignment between the front and rear flanges 44 and 46, while a shoulder bolt 70 held within threaded apertures passing through the bevel surface areas 50 of the support members 48 and through corresponding perforations in the margins of plate 58 releasably secure the radiation shield assembly 56 in place.

The treatment reel 42 further includes an annular, toothed reel gear 72 suitably mounted on the back of the rear flange 46 which has a plurality of gear teeth 74 on the inner periphery thereof that are adapted to meshingly engage a later discussed drive gear 76. Reel gear 72 further includes a plurality of circumferentially spaced, longitudinally extending apertures 78 therethrough radially aligned with the radiation shield assemblies 56 and adapted to receive therewithin a plunger 80 associated with a later discussed solenoid operated locking device 82. The reel gear 72 is provided with a plurality of longitudinally and outwardly extending actuating nodes 84 circumferentially spaced at regular intervals with respect to the radiation shield assemblies 56.

The treatment head 36 has a suitable source of radiation 86 mounted centrally therewithin, around which source a keyhole shaped layer of radiation shielding material 88 may be provided to avoid undesirable escape of radiation therefrom. The shielding material 88 includes a conically shaped cavity 90 therewithin placing an area in the periphery of the cylindrically shaped treatment head 36 in communication with the radiation source 86. As best seen in FIGS. 1 and 2, the cavity 90 permits radiation from the radiation source 86 to be directed through the radiation beam opening 92 in the head 36, thence through one of the reel openings 59 and corresponding radiation shield assembly 56 in registration with the beam opening 92 to a patient disposed on the platform 24, in alignment with the radially extending axis 94. Suitable means may be provided including beam collimating means (not shown) for limiting the cross-sectional area of the radiation beam passing through the opening 92 to the cross-sectional area of the radiation shield 60 in order to prevent undesired escape of radiation around the outer perimeter of the radiation shield 60.

The treatment head 36 includes a stairstep, annular, cut-out area in the periphery thereof which forms a first reel-receiving notch 96 therein for receiving the support members 48, rear flange 46, and reel gear 72, and further forms a second reel-receiving notch 98 for receiving the inner periphery of the front flange 44. A plurality of reel loading ball elements 100 suitably secured to the treatment head 36 at circumferentially spaced locations around the periphery of the latter and aligned with the V-shaped grooves 52, extend into the first reel-receiving notch 96 and are in communication with the V-shaped grooves 52 and 57. As will become apparent later, ball elements 100 in combination with the V-shaped grooves 52 provide a means for guiding the reel 42 onto the head 36. Treatment head 36 has three, recessed areas 102 in the outer periphery thereof, circumferentially spaced approximately 120° apart from each other. Means for releasably holding and supporting the reel 42 on the head 36 in the nature of a reel-supporting, roller assembly mounted within each of the recessed areas 102 includes a pair of longitudinally spaced roller members 104 and 106 respectively received within corresponding, annular channels provided in the associated flanges 44 and 46, and rotatably mounted on opposite extremities of an inclined axle element 108. Axle element 108 includes an enlarged central portion having a threaded aperture therethrough for threadably receiving an outwardly extending, threaded output shaft 110 of a selectively energizable motor means 112 adapted, when energized, to selectively rotate the output shaft 110 in either rotational direction. A stabilizing link 114 has the opposite extremities respectively pivotally coupled to the treatment head 36 and central portions of the axle element 108 in order to prevent rotation of the latter with respect to output shaft 110 upon rotation of the latter, it being understood that the pivotal mounting of the stabilizing link 114 include provision for lost motion to allow free reciprocal movement of the axle element 108. Means for rotating the treatment reel 42 relative to the treatment head 36 are provided which include a drive gear 76 meshingly engaging the gear teeth 74 associated with the reel gear 72, drive gear 76 being secured on the rotatable output shaft 116 of a motor means 118, such as an ordinary electric motor, which is mounted within a recessed portion 120 of the treatment head 36. Means for preventing the rotation of the treatment reel 42 relative to the treatment head 36, and for locking one of the radiation shield assemblies 56 in registration with the opening 92, are provided in the nature of a motor device 82, such as a solenoid, mounted within the recessed portion 120 and having a reciprocating output shaft 80 which is selectively insertable into the aperture 78 of the reel gear 72.

Means for sensing the position of the reel 42 relative to the head 36 and for controlling the operation of the motor means 118 to produce rotation of the reel 42 relative to the head 36 includes an electrical switch 122 secured to the treatment head 36 and having a switching element thereof connected to one extremity of a link element 124, the opposite extremity of the latter having rotatably mounted thereon an engagement wheel 126. Link element 124 is normally biased to shift the engagement wheel 126 into the space 128 between the treatment head 36 and reel gear 72 a sufficient distance to allow engagement therewith by the actuating nodes 84 upon rotation of the treatment reel 42.

Prior to discussing the method of treatment using the cineradiotherapy system 20, a description of the procedure in which treatment reels 42 are installed and removed from the treatment head 36 will first be provided. Let it first be assumed that the treatment head 36 does not have a treatment reel 42 mounted thereon and that it is desired to install such reel 42 in preparation for the treatment of a patient. The reel 42 is first positioned adjacent the cineradiotherapy device 26 in a standby position adjacent the latter while the device 26 is actuated to rotate the gantry 34, and thus the treatment head 36, until the latter is disposed at approximately a four-O'clock position with respect to the horizontal axis 32, as shown in FIG. 3. For convenience, a wheeled transportation cart (not shown) adapted for supporting one of the reels 42 at a suitable height for loading onto the treatment head 36 may be employed, and assuming such a cart or the like is being used, the V-shaped openings 54 in the rear flange 46 are aligned with, and positioned immediately adjacent to the corresponding ball elements 100, whereupon the cart (not shown) may be shifted in a manner to slide the open, rear end of the treatment reel 42 onto the treatment head 36. As the reel 42 is shifted onto the treatment head 36, the ball elements 100 are received within and engageably support the V-shaped grooves 52 in the support members 48, at the nine-O'clock, twelve-O'clock, and three-O'clock positions on the treatment reel 42 thereby reliably guiding and supporting the latter on the treatment head 36. The treatment reel 42 is shifted rearwardly onto the treatment head 36 until the annular channels in the front and rear flanges 44 and 46 are in radial alignment with the corresponding roller members 104 and 106; at this point the ball elements 100 are placed in communication with the annularly extending, V-shaped grooves 57 in each of the support members 48. Motor means 112 may then be energized to produce rotation of the output shaft 110 in a manner to shift the axle element 108 radially outward thereby shifting the roller members 104 and 106 into the channels respectively associated with the front and rear flanges 44 and 46. With the treatment reel 42 thus installed, the latter is supported for rotation about the treatment head 36 by means of the front and rear flanges 44 and 46 which are carried upon the roller members 104 and 106. The motor means 118 may then be energized to rotate the drive gear 76 which in turn drives the reel gear 72 to produce rotation of the treatment reel 42 relative to the treatment head 36. Normally, once activated, motor means 18 will produce rotation of the treatment reel 42 until one of the actuating nodes 84 engages the wheel 126 to actuate the switch 122 whereupon motor means 118 will be energized and the motor device 82 will be actuated to extend the plunger 80 into one of the apertures 78 aligned therewith. With the plunger 80 inserted into the aperture 72 it can be appreciated that the treatment reel 42 is securely locked in place and is substantially prevented from any rotational movement whatsoever. The number of apertures 78 and actuating nodes 84 correspond to the number of radiation assemblies 56 employed and are circumferentially spaced relative to each other in a manner to position one of the radiation shield assemblies 56 in alignment with the opening 92 upon successive actuations of the motor means 118. With the plunger 80 disposed within one of the apertures 78, successive energization of the motor means 118 results in deactuation of the motor device 82 and retraction of the plunger 80 to allow rotation of the treatment reel 42 until the next in the series of actuating nodes 84 produces operation of the switch 122 to deenergize the motor means 118 and actuate the motor device 82.

Although not specifically disclosed herein, the cineradiotherapy device 26 will include control means for successively rotating the treatment head 36 between a number of discrete, radial treatment positions about the horizontal axis 32, the number of such treatment positions corresponding to the number of radiation shield assemblies 56 carried by the treatment reel 42, and it may be appreciated that twelve radial treatment positions, spaced 30° apart, will be employed in connection with the preferred form of the invention disclosed herein, inasmuch as twelve radiation shield assemblies 56 are carried by the reel 42. Clearly, however, the number of radiation shield assemblies 56 employed in connection with the present invention will be dictated by the circumference of the treatment reel 42 and may vary in accordance with particular applications. In fact, obviously a fewer number of radiation shield assemblies 56 may be employed in connection with the treatment reel 42 disclosed herein, although as will become later apparent, it will generally be desirable to employ a maximum number of such radiation shield assemblies 56.

Assuming now that treatment has been completed of a particular volume of tissue in an individual patient, and that it is desired to treat a differently configured volume of tissue in the same patient, or in a different patient, the treatment reel 42 must be removed from the treatment head 36 and replaced with another treatment reel having radiation shield assemblies 56 particularly adapted for treatment of such other volume of tissue. In order to remove the treatment reel 42, the gantry 34 and treatment head 36 are rotated about the horizontal axis 32 until the treatment head 36 assumes the four-O'clock loading position depicted in FIG. 3. If desired, the previously mentioned transportation cart may be disposed beneath the treatment reel 42 and in supporting relationship to the latter when the reel 42 is delivered to the loading position shown in FIG. 3. The treatment reel 42 is then rotated until the V-shaped grooves 52 are in aligned, longitudinal registration with the corresponding ball elements 100 when the treatment head 36 is disposed in the loading position shown in FIG. 3. The motor means 112 may then be actuated to shift the axle element 108 radially inward, thereby likewise shifting the roller members 104 and 106 inwardly away from the corresponding front and rear flanges 44 and 46 and in clearing relationship to each of the latter. With the weight of the treatment reel 42 being supported by a transportation cart or the like, the reel 42 may be shifted outwardly away from the treatment head 36, over the ball elements 100, and the reel 42 may be moved away from the treatment area while a second treatment reel 42 associated with the treatment of a different volume of tissue in a patient may then be installed on the treatment head 36 in a manner similar to that described previously.

Having thus described the general operational characteristics of the cineradiotherapy device 26, attention is now turned to a discussion of a novel method of radiotherapy treatment employing the cineradiotherapy system 20. It is first necessary to determine the precise geometrical configuration of the tumor volume within the patient to be treated, as well as the position of such tumor volume within the patient's body. This may be accomplished using conventional radiographic methods and reconstruction procedures such as axial transverse multisection radiography and stereosynthesis in order to produce a three dimensional representation of the tumor. Having thus determined the exact volume and configuration of the tumor, a plurality of the radiation shield assemblies 56 are then custom fabricated for treatment of the particular tumor involved. More particularly, the radiation shields 60 are fabricated in accordance with the method disclosed in U.S. Pat. No. 3,937,971 with the cut-out portions 62 therein corresponding to various profiles of the tumor involved as viewed from various points on the circumference of a reference circle lying in a plane passing transversely through the mentioned tumor. Consequently, with respect to the treatment reel 42 disclosed herein having twelve of the radiation shield assemblies 56 mounted thereon, it can be appreciated that the cut-out portion 62 in such shield assemblies 56 correspond to twelve different profiles of the particular tumor to be treated. Similarly, in the event that it is desired to protect a vital, healthy organ in the patient which lies between the source of radiation 86 and the tumor to be treated, a plurality of central radiation absorbers 64 may also be manufactured, in accordance with the method disclosed in U.S. Pat. No. 3,937,971, with the cross-sectional configuration thereof corresponding to the various profiles of such organ, as viewed from various points on the above discussed reference circle lying in the mentioned plane passing transversely through the tumor. Having manufactured both the radiation shield 60 and central radiation absorber 64, each of the latter are mounted, using screws or the like, on the support plate 58 thereby completing fabrication of the radiation shield assembly 56. Each of the radiation shield assemblies 56 are then mounted on the treatment reel 42 in a prescribed, consecutive order, normally corresponding to the order of the view points lying around the circumference of the mentioned reference circle surrounding the tumor.

Each of the radiation shield assemblies 56 is mounted in the corresponding position on the treatment reel 42 by positioning the edges of the support plate 58 within the slots 68 in the front flange 44 on opposite sides of the cut-out portion 66, and the assembly 56 is then slid longitudinally, rearward through the slots 53 until the rear edge of the plate 58 contacts the front side of the rear flange 46, whereupon the shoulder bolts 70 may be inserted into support members 48 whereby to securely hold each of the assemblies 56 in place on the treatment reel 42, in aligned, side-by-side relationship to each other. The above described procedure of mounting the assemblies 56 on the treatment reel 42 may be performed when the latter is removed from the treatment head 36, or alternatively, it may be convenient to first mount the treatment reel 42 on the treatment head 36, as shown in FIG. 3, in order to allow automatic rotation of the reel 42 as the assemblies 56 are successively mounted thereon.

In any event, after each of the assemblies 56 is mounted on the reel 42 and the latter is installed on the treatment head 36 in the manner previously described, the treatment of a tumor volume of tissue in a patient is ready to commence. The patient is first placed on the upper side of the platform 24 of the treatment table 22, with the tumore volume transversely aligned with a vertical plane which will subsequently be traced by the radial axis 94, and axially aligned with the horizontally extending axis 32; for alignment purposes, the position of such tumor volume may be adjusted by laterally or elevationally shifting the platform 24 using mechanism of the treatment table 22 particularly designed for this purpose. With the tumor volume thus aligned at the intersection point 130 of the axes 32 and 94, the gantry 34 is then rotated to a starting position whereat the profile presented by the tumor volume to the source of radiation 86 coincides with the configuration of the cut-out portion 62 in one of the radiation shields 60 mounted on the treatment reel 42. For purposes of the present illustration, let it be assumed that the position of the gantry 34 as depicted in FIG. 1 coincides with the starting position, with the source of radiation 86 vertically aligned above the intersection point 130. With the treatment head 36 rotated to such starting position, motor means 118 is then actuated to rotate the treatment reel 42 with respect to the head 36 until the radiation shield assembly 56 having cut-out portions 62 therein corresponding to such starting position is shifted into a shielding position aligned with the beam opening 92 and interposed between the source of radiation 86 and the tumor volume. At this point, the gantry 34 is rotated in one angular direction toward the next treatment starting position, and the radiation source 86 is activated to produce a prescribed dosage of radiation, which radiation is delivered through the cavity 90 onto the radiation shield 60, which functions, by virtue of the latter's cut-out portions 62, to shape the resulting radiation beam emanating from the treatment head 36, whereby the cross-sectional configuration of the latter conforms to the profile of the tumor presented to the radiation source 86. As radiation is being delivered from the source 86 thereof to the tumor, the central radiation absorber 64, which is of "full thickness" in distinction to prior types thereof, virtually completely shields, and thereby protects, a vital, healthy organ disposed within the path of the radiation beam. After application of the radiation dosage to the first tumor profile and prior to initiating the application of radiation from the second treatment starting position, which coincides with the first treatment ending position, motor means 118 is energized to again rotate treatment reel 42 with respect to head 36 in order to move a second radiation shield assembly 56 into the shielding position aligned with the beam opening 92 between the radiation source and the tumor. Again the gantry 34 is rotated toward the next treatment starting position, and the source 86 is activated to deliver a prescribed dosage to the second treatment profile corresponding to the cut-out portions 62 in a second one of the radiation shields 60, while similarly, a second profile of a healthy organ to be protected is presented to the radiation source 86 which corresponds to the central absorber 64 associated with the mentioned second radiation shield 60. Normally, the radiation shield assemblies 56 will be mounted on the reel 42 in a prescribed order which allows sequential shifting of adjacent shield assemblies 56 into shielding position adjacent the opening 92 as the gantry 34 and head 36 are rotated about the axis 32 to each of the treatment positions. Thus, with respect to the preferred embodiment disclosed herein, it can be appreciated that twelve discrete dosages of radiation are applied to different profiles of the tumor as the treatment head 36 shifts between twelve discrete treatment starting positions around such tumor, in a manner to provide a treatment technique which I have termed "cineradiotherapy".

Normally then, treatment of a tumor in a patient is completed upon a complete rotation of the treatment head 36 and one complete revolution of the treatment reel 42. After completion of a radiotherapy treatment session, the treatment reel 42 may be simply removed and placed in storage while another reel may be installed for treatment of the next patient in the manner previously described.

From the foregoing description of the unique method of cineradiotherapy using the novel cineradiotherapy system, it is clearly apparent that the need for complicated mechanism for producing continuous, synchronous shielding of healthy tissues is obviated. Moreover, due to the fact that the specially configured shielding assemblies may be rapidly installed and removed from the cineradiotherapy device, it is apparent that a high volume of patients may be treated with a single cineradiotherapy device, in contrast to the prior art conformation radiotherapy apparatus which required comlex interchange of shielding mechanisms to accommodate sequential treatment of various patients.

INDUSTRIAL APPLICABILITY

The construction details and mode of operation of the cineradiotherapy device have been made amply clear by the foregoing description thereof. Those skilled in the art of conformation radiotherapy will readily appreciate that the novel treatment method disclosed herein may be also practiced by maintaining the radiation source 86 at a fixed location while the patient (and thus the tumor) are rotated with respect to such radiation source 86 to present the various profiles of the tumor to such radiation source. Thus, it is clear the present method may be practiced merely by producing relative rotational motion between the tumor volume and the radiation source.

From the foregoing, it is apparent that the invention provides an effective device implemented method for performing conformation radiotherapy which not only conformally imparts uniform radiation to the volume of tissue defined by the tumor, but also provides enhanced radiation protection of vital, healthy organs disposed within the path of the radiation beam. Thus, it will be observed that the method and apparatus disclosed herein not only provide for the reliable accomplishment of the object of the invention, but do so in a particularly simple and economical manner. It is recognized, of course, that those skilled in the art may make various modifications or additions to the preferred embodiment chosen to illustrate the invention without departing from the gist and essence of this contribution to the art. Accordingly, it is to be understood that the protection sought and to be afforded hereby should be deemed to extend to the subject matter claimed and all equivalents thereof fairly within the scope of the invention.

Having thus described the invention, what is claimed as new and desired to be secured by Letters Patent is:

1. A method for providing radiation therapy treatment of a volume of living tissue in a patient, including the steps of:
    shifting a source of radiation between spaced treatment locations in a course around said volume of tissue;
    sequentially interposing each of a plurality of individual, separate radiation beam shaping shields into a shielding position between said tissue volume and said radiation source whereby a different one of said shields is interposed into said shielding position when said source is disposed at each of said treatment locations in said course; and applying a dosage of radiation from said source thereof through said beam shaping shields to said volume of tissue only when said radiation source is disposed at one of said treatment locations.

2. The invention of claim 1 wherein:
said shifting step is performed by rotating said radiation source around said volume of tissue in said course, and
said shield interposing step is performed by rotating said plurality of said shields around said radiation source.

3. A method for protecting a quantity of living tissue having a prescribed geometrical shape from radiation applied to a volume of tissue surrounding said quantity of tissue thereof during conformation radiotherapy of cancer or the like in a patient, including the steps of:
shifting a source of radiation between a plurality of spaced treatment locations in a path of travel around said volume of tissue;
successively interposing each of a plurality of different radiation shields, one corresponding to each of said treatment locations, and each having a shielding configuration corresponding to the profile of said quantity of tissue presented to said radiation source at the corresponding treatment location into a shielding position between said quantity of tissue and said radiation source, whereby a different one of said radiation shields is disposed in said shielding position at each of said treatment locations; and
applying a dose of radiation from said source thereof to said volume of tissue only when said radiation source is disposed at one of said treatment locations, said radiation shields being operative to prevent radiation from reaching each of the profiles of said quantity of tissue presented to said radiation source during said applying step whereby to protect said quantity of tissue from said radiation.

4. The invention of claim 3, wherein:
said shifting step is performed by rotating said radiation source around said volume of tissue, and
said shield interposing step is performed by sequentially rotating said shields into said shielding position.

5. A method of protecting a portion of living tissue from radiation applied to a volume thereof surrounding said portion during conformation radiotherapy treatment of a patient, including the steps of:
(A) providing a first radiation shield having a cutout area therein corresponding in shape to one profile of said volume;
(B) providing a second radiation shield corresponding in shape to one profile of said tissue portion to be protected and having a sufficient thickness to essentially completely prevent the passage of radiation therethrough;
(C) interposing said first and second shields into a shielding position between said volume of tissue and said radiation source with said second shield aligned in a path extending between said tissue portion and said cutout area of said first shield;
(D) applying a dose of radiation from said source thereof through said cutout area of said first shield to said volume of tissue;
(E) producing relative rotational movement between said volume of tissue and said radiation source whereby to present another profile of said tissue volume and of said portion thereof to said radiation source;
(F) providing a third radiation shield having a cutout area therein corresponding in shape to said another profile of said tissue volume;
(G) providing a fourth radiation shield corresponding in shape to said another profile of said tissue portion and having a sufficient thickness to essentially completely prevent the passage of radiation therethrough;
(H) interposing said third and fourth shields into a shielding position between said volume of tissue and said radiation source with said fourth shield aligned in a path extending between said tissue portion and said cutout area of said third shield;
(I) applying a dose of radiation from said source thereof through said cutout area in said third shield to said volume of tissue; and
(J) repeating steps (E) through (I) using additional radiation shields corresponding to still further profiles of said volume of tissue and said portion thereof until essentially all the tissue in said volume thereof except said protected portion thereof has been treated with radiation.

6. The invention of claim 5, wherein:
steps (C) and (H) are performed by sequentially rotating said radiation shields into said shielding position, and
step (E) is performed by rotating said radiation source in a course around said volume of tissue.

7. The invention of claim 6, wherein:
steps (C) and (H) are each performed by rotating said shields in a path around said radiation source, and
steps (D) and (I) are each performed only when a profile of said tissue volume and of said portion thereof corresponding to one associated pair of said shields is presented to said radiation source.

8. Improved radiotherapy apparatus of the type including a source of radiation adapted to be directed onto a patient through radiation shield means for shaping a field of radiation conforming to a volume of tissue in said patient having a prescribed geometrical configuration, and means for rotating said radiation source around said patient including means for supporting said radiation source, wherein the improvement includes:
drum shaped structure rotatably mounted on said supporting means with said radiation source disposed therewithin,
said structure including open areas in the circumferential sidewalls thereof placing said radiation source in communication with said patient,
said structure being adapted to have a plurality of discrete, separate radiation shields mounted on said sidewalls thereof in superimposed relationship to said open areas of the latter; and
means operably coupled with said drum shaped structure for causing the latter to rotate about its longitudinal axis whereby to shift each of said radiation shields into or out of a beam of radiation delivered from said source thereof through said open areas in said sidewalls to said volume of tissue in said patient.

9. The invention of claim 8, wherein said longitudinal axis of said drum structure is essentially horizontal and there is further provided:
means carried by said supporting means for releasably holding said drum structure on said supporting means; and means for releasably securing each of said radiation shields on said drum structure.

10. The invention of claim 9, wherein there is further provided:
means on said drum structure and said supporting means for guiding the former onto the latter during mounting of said drum structure on said supporting means; and
means on said drum structure and said supporting means for sensing the position of said open areas in said sidewalls of said drum structure relative to said beam of radiation.

11. The invention of claim 10, wherein:
said rotating means includes a selectively energizable motor member mounted on said supporting means and having an output shaft thereof operably coupled with said drum structure for rotating the latter when said motor member is energized,
said motor member being operably coupled with said position sensing means and selectively energizable in response to the operation of the latter, and
said releasable holding means includes a plurality of selectively shiftable guide mechanisms disposed adjacent the circumferential sidewalls of said drum shaped structure at circumferentially spaced locations of the latter,
each of said guide mechanisms including a guide member shiftable into and out of slidable engagement with said drum structure.

12. The invention of claim 11, wherein there is further provided means operatively associated with said motor member and with position sensing means for selectively locking said drum structure against rotation with respect to said supporting means, and
said releasable securing means includes a pair of longitudinally extending holding slots in said drum structure on opposite sides of each of said open areas in the latter for slidably receiving and holding portions of said radiation shields therein,
said guide means including a plurality of circumferentially spaced, longitudinally extending grooves in said drum structure and a plurality of corresponding guide elements carried by said supporting structure and slidably receivable within said longitudinally extending grooves, said drum structure further including circumferentially extending groove means in the circumferential sidewalls thereof communicating with said guide elements for providing clearance of the latter upon rotation of said drum structure.

13. Radiotherapy apparatus, including:
a source of radiation adapted to direct a beam of radiation onto a patient to be treated;
means coupled with said radiation source for causing said radiation beam to rotate in a course around said patient;
a plurality of discrete, separate radiation shields each provided with a cutout portion therein through which radiation may pass,
said cutout portions of said shields having respective geometrical configurations corresponding to different profiles of a volume of tissue in said patient to be treated with radiation;
means mounting said plurality of radiation shields for shifting with respect to said radiation beam path; and
means coupled with said shiftable mounting means for driving the latter to sequentially shift each of said radiation shields into a shielding position within said path and between said tissue volume and said radiation source as said radiation beam rotates about said patient whereby to permit application of radiation from said source thereof to said tissue volume from selective locations in said rotational course corresponding to said profiles.

14. The invention of claim 13, wherein at least certain of said radiation shields each include a radiation absorbing member disposed within the cutout portion of the respectively associated shield, each of said absorbing members presenting a shape to radiation passing through the cutout portion of the respectively associated shield corresponding to a profile of a quantity of tissue in said patient adjacent said volume thereof which is to be protected from radiation, said absorbing member comprising a radiation absorbing material having a thickness extending in the direction of said beam path sufficient to essentially completely prevent passage of radiation therethrough.

15. The invention of claim 14, wherein there is further provided:
a plurality of essentially planar mounting members respectively associated with each of said radiation shields and comprising a material suitable for allowing radiation to pass therethrough,
each of said radiation shields, including said radiation absorbing members associated with said certain of said shields, being secured on one side of a respectively associated mounting member.

16. The invention of claim 14, wherein said shiftable mounting means includes:
support structure including a head portion having said radiation source mounted therein and adapted to rotate around said patient, and
a generally cylindrical reel portion rotatably carried by said head portion and having said radiation source disposed therewithin,
said reel portion including open areas in the circumferential sidewalls thereof through which radiation may pass when said areas are interposed between said radiation source and said patient,
said radiation shields being carried in aligned, side-by-side relationship with each other on said sidewalls of said reel portion in superimposed relationship to said open areas in the latter.

17. The invention of claim 16, further including:
means intercoupling said reel portion and said head portion for releasably holding the former on the latter;
means coupled with said reel portion for releasably securing each of said radiation shields on said reel portion; and
means intercoupling said reel portion and said head portion for guiding the former onto the latter during mounting of said reel portion on said head portion,
said driving means including a motor member mounted on said head portion and having an output shaft coupled with said reel portion for rotating the latter with respect to said head portion.

18. The invention of claim 17, including:
means mounted on said head portion and operably coupled with said reel portion for sensing the position of said radiation shields relative to said beam path; and
means operatively associated with said motor member and said sensing means for selectively locking said reel portion from rotation when a selected one of said shields is shifted into said shielding position.

* * * * *